United States Patent
Merkel et al.

(10) Patent No.: US 8,373,010 B2
(45) Date of Patent: Feb. 12, 2013

(54) METHODS TO PRODUCE 3,3,3-TRIFLUOROPROPENE

(75) Inventors: Daniel C. Merkel, Orchard Park, NY (US); Konstantin A. Pokrovski, Orchard Park, NY (US); Hsueh Sung Tung, Getzville, NY (US); Selma Bektesevic, Williamsville, NY (US)

(73) Assignee: Honeywell International Inc., Morristown, NJ (US)

( * ) Notice: Subject to any disclaimer, the term of this patent is extended or adjusted under 35 U.S.C. 154(b) by 266 days.

(21) Appl. No.: 12/875,170

(22) Filed: Sep. 3, 2010

(65) Prior Publication Data

US 2012/0059201 A1 Mar. 8, 2012

(51) Int. Cl.
*C07C 17/25* (2006.01)

(52) U.S. Cl. ........ 570/156; 570/155; 570/157; 570/158; 570/160

(58) Field of Classification Search .......... None
See application file for complete search history.

(56) References Cited

U.S. PATENT DOCUMENTS

| | | | |
|---|---|---|---|
| 2,889,379 | A | 6/1959 | Ruh et al. |
| 6,211,421 | B1 | 4/2001 | Elsheikh et al. |

FOREIGN PATENT DOCUMENTS

| | | |
|---|---|---|
| CN | 101074185 A | 11/2007 |
| CN | 101306978 A | 11/2008 |
| GB | 2464535 A | 4/2010 |
| WO | 2008045910 A1 | 4/2008 |
| WO | 2009003157 A1 | 12/2008 |

OTHER PUBLICATIONS

Wang, Bo, et al., Synthesis of 3,3,3-trifluoropropene-1 by Gaseous Phase Catalytic Fluorination, Xian Modern Chemistry Research Institute, Yingyong Huagong (2007), 36(7), 638-640, Peoples Republic of China (English translation of Abstract included).

*Primary Examiner* — Brian J Davis
(74) *Attorney, Agent, or Firm* — Bruce O. Bradford

(57) ABSTRACT

Disclosed is a process for the preparation of 3,3,3-trifluoropropene comprising the steps of; (1) fluorination of 240fa to form 245fa; (2) conversion of 245fa to a cis/trans mixture of 1234ze; (3) hydrogenation of the cis/trans mixture of 1234ze to form 254fb ; and (4) dehydrofluorination of 254fb to produce 3,3,3-trifluoropropene. Alternatively or additionally, a second process for the preparation of the desired compound comprises the following steps; (1) fluorination of HCC-240fa to form HCFC-244fa; (2) conversion of 244fa to a cis/trans mixture of HFO-1234ze; (3) hydrogenation of the cis/trans mixture of 1234ze to form HFC-254fb; and (4) dehydrofluorination of 254fb to produce 3,3,3-trifluoropropene.

32 Claims, No Drawings

METHODS TO PRODUCE 3,3,3-TRIFLUOROPROPENE

FIELD OF THE INVENTION

The current invention describes methods to produce 3,3,3-trifluoropropene (TFP or HFO-1243zf), a commercially available monomer that starts with a relatively inexpensive chlorinated hydrocarbon as the organic raw material. The processes described herein involve up to four reaction steps depending on which raw materials are most readily available and/or least expensive.

BACKGROUND OF THE INVENTION

The current invention is more cost effective than the current commercial process to produce TFP because it makes use of by-products from processes used to prepare trans-1234ze (trans-1,3,3,3-tetrafluoropropene) as an intermediate. See for example, U.S. Pat. No. 7,709,691 and U.S. Patent Publication Nos. 2009/0270660 and 2008/0103342, the disclosures of which are hereby incorporated herein by reference.

SUMMARY OF THE INVENTION

One embodiment of the present invention is a method to produce HFO-1243zf comprising the steps of:
(1) fluorination of HCC-240fa to form HFC-245fa;
(2) conversion of HFC-245fa to a cis/trans mixture of HFO-1234ze;
(3) hydrogenation of the cis/trans mixture of 1234ze to form HFC-254fb; and
(4) dehydrofluorination of 254fb to produce HFO-1243zf.

Another embodiment of the present invention is a method to produce HFO-1243zf comprising the steps of:
(1) fluorination of HCC-240fa to form HCFC-244fa;
(2) conversion of 244fa to a cis/trans mixture of HFO-1234ze;
(3) hydrogenation of the cis/trans mixture of 1234ze to form HFC-254fb; and
(4) dehydrofluorination of HFC-254fb to produce HFO-1243zf.

These processes may be conducted in separate reactors until common intermediates have been formed, and where after the processes may be combined to produce the desired compound. Alternatively, these processes can be conducted in the same reactor, at different stages, using the specific reactants and conditions described in greater detail below. As described in detail below, the starting materials employed herein can comprise various mixtures of compounds, particularly when recovered as byproducts of other reactions.

DETAILED DESCRIPTION OF THE INVENTION

As described above, one embodiment of the process of the present invention involves four steps. The first step uses HCC-240fa as a raw material. In the presence of $SbCl_5$ and HF, HCC-240fa is converted to HFC-245fa, as shown below in equation (1):

(1)

As equation (1) illustrates, HFC-245fa is formed by the fluorination of HCC-240fa with HF in the presence of a fluorination catalyst. This reaction is preferably conducted at a temperature of from about 60° C. to about 140° C. and at a pressure of from about 50 to about 300 psig. The reaction is preferably conducted in the presence of a suitable pentavalent antimony fluorination catalyst. Such pentavalent antimony compounds may be antimony halides, mixed pentavalent antimony halides, or a mixture of pentavalent antimony halides. More preferably the catalyst is antimony pentachloride ($SbCl_5$) or antimony pentafluoride ($SbF_5$), most preferably antimony pentachloride.

Alternatively in the presence of $TiCl_4$ and HF, HCFC-244fa is formed as shown below in equation (2):

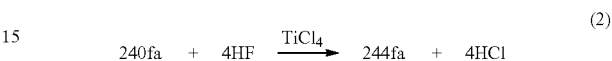
(2)

As equation (2) illustrates, HFC-244fa is formed by the fluorination of HCC-240fa with HF in the presence of a fluorination catalyst. This reaction is preferably conducted at a temperature of from about 85° to about 120° C. and at a pressure of from about 80 to about 140 psig. A preferred fluorination catalyst for reaction (2) is titanium tetrachloride (liquid under ambient conditions) which has been partially or totally fluorinated by the action of anhydrous HF. Additional fluorination catalysts that can be used include $SnCl_4$, $TaCl_5$, $SbCl_3$, $FeCl_3$, and $AlCl_3$ which have been partially of totally fluorinated by the action of anhydrous HF.

Both reactions (1) and/or (2) can be carried out in a batch reactor. Alternatively, these reactions can be carried out in a Continuously Stirred Tank Reactor (CSTR). Using a condenser, the reaction products 245fa or 244fa, HCl, and HF can be separated. HF can then be recycled back to reactor while HCl is collected.

The second step involves the formation of a cis/trans mixture of HFO-1234ze. One of the routes to make the cis/trans mixture of 1234ze is to carry out reaction in the presence of KOH, as shown below in equations (3) and (4):

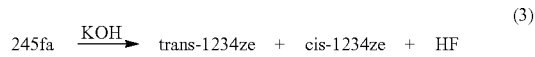
(3)

(4)

As equations (3) and (4) illustrate, a cis/trans mixture of HFO-1234ze is formed by either the dehydrochlorination of HCFC-244fa and/or the dehydrofluorination of HFC-245fa.

For reactions (3) and (4) one can carry out the reactions in either a batch reactor or a CSTR. Alternatively, solid KOH can be used. Other metal hydroxides such as NaOH, LiOH, $Mg(OH)_2$, $Ca(OH)_2$, or CaO can be used instead of KOH.

In the preferred embodiment of the invention, the dehydrochlorination of HCFC-244fa and dehydrofluorination of HFC-245fa are accomplished by reacting each of these respective intermediates with a strong caustic solution (i.e., pH greater than 10) that includes, but is not limited to KOH, NaOH, LiOH, $Mg(OH)_2$, $Ca(OH)_2$, and CaO at an elevated temperature.

In the preferred embodiment of the invention, the caustic strength of the caustic solution is of from about 2 wt % to about 65 wt %, more preferably from about 5 wt % to about 52 wt % and most preferably from about 10 wt % to about 45 wt %. The reaction is preferably conducted at a temperature of from about 20° C. to about 100° C., more preferably from about 30° C. to about 90° C. and most preferably from about 40° C. to about 80° C. The reaction is preferably conducted at atmospheric pressure, super-atmospheric pressure or under vacuum. The vacuum pressure can be from about 5 torr to about 760 torr. In addition, a phase transfer agent may optionally be used to help facilitate the reaction. This optional step may be conducted using solvents that are well known in the art for said purpose.

The second step can also be accomplished using catalyst such as fluorinated $Cr_2O_3$ or CsCl on $MgF_2$. The use of solid catalyst allows the use of packed bed reactor. Equations (5) and (6) describe formation of cis- and trans-1234ze from 245fa and 244fa:

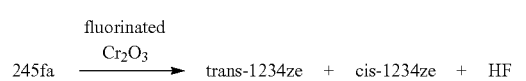

(5)

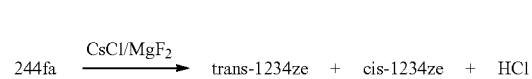

(6)

As equations (5) and (6) illustrate, HFO-1234ze is formed by the dehydro-chlorination of HCFC-244fa and the dehydrofluorination of HFC-245fa.

In the preferred embodiment of the invention, the dehydrochlorination of HCFC-244fa and dehydrofluorination of HFC-245fa are accomplished by reacting at an elevated temperature by thermal decomposition in the presence of a catalyst. The preferred temperatures for the thermal decomposition are from about 30° C. to about 550° C., more preferably from about 300° C. to about 550° C. As above, the reaction is preferably conducted at atmospheric pressure, super-atmospheric pressure or under vacuum. The vacuum pressure can be from about 5 torr to about 760 torr.

The reaction for the dehydrofluorination of HFC-245fa (5) is conducted in the presence of a dehydrofluorinating catalyst which may be one or more of fluorinated metal oxides in bulk form or supported, metal halides in bulk form or supported, and carbon supported transition metals, metal oxides and halides. Suitable catalysts include fluorinated chromia (fluorinated $Cr_2O_3$), fluorinated alumina (fluorinated $Al_2O_3$), metal fluorides (e.g., $CrF_3$, $AlF_3$) and carbon supported transition metals (zero oxidation state) such as Fe/C, Co/C, Ni/C, Pd/C.

As shown in equation (6), the reaction for the dehydrochlorination of HCFC-244fa is also conducted in the presence of a catalyst. Preferred catalyst in step comprises one or more of supported or bulk metals of Pd, Pt, Rh, Fe, Co, Ni, Cu, Mo, Cr, Mn, magnesium halides, calcium halides, lithium halides, sodium halides, potassium halides, cesium halides, cerium halides, yttrium halides, aluminum halides, halogenated magnesium oxides, halogenated calcium oxides, halogenated barium oxides, halogenated zinc oxides, halogenated cesium oxides, halogenated aluminum oxide, and combinations thereof.

More preferred catalysts for use in reaction (6) comprise one or more of supported or bulk catalysts selected from the group consisting of MgO, CaO, BaO, ZnO, CsO, $Al_2O_3$, LiF, NaF, KF, CsF, $MgF_2$, $CaF_2$, LiCl, NaCl, KCl, $CeF_4$, $FeF_3$, $YF_3$, $AlF_3$ and CsCl. The most preferred catalyst for use in reaction (6) comprises a combination of CsCl and MgO, or a combination of CsCl and $MgF_2$.

The third step of the process of the invention is the hydrogenation of cis- or trans-HFO-1234ze to form HFC-254fb. This reaction can be accomplished in the presence of catalyst such as Pd on Carbon. Other catalysts include $Pd/Al_2O_3$, Ni/C, or $Ni/Al_2O_3$. Reactions to form 254fb from cis- or trans-1234ze are depicted in equations (7) and (8):

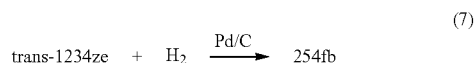

(7)

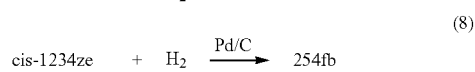

(8)

As equations (7) and (8) illustrate, HFC-254fb is formed by the hydrogenation of either cis-1234ze or trans-1234ze. In the preferred embodiment of the invention, the hydrogenation of either cis-1234ze or trans-1234ze is accomplished by reacting at an elevated temperature and in the presence of a hydrogenation catalyst. The preferred temperature for the hydrogenation is about 50° C. to about 400° C. and a pressure of 0 psig to 500 psig.

The last step of the process involves conversion of 254fb to TFP. This reaction can be accomplished using reagents such as KOH, NaOH, LiOH, $Mg(OH)_2$, $Ca(OH)_2$, and CaO. The reaction is depicted by equation (9):

(9)

As equation (9) illustrates, TFP (HFO-1243zf) is formed by the dehydro-fluorination of HFC-254fb. In the preferred embodiment of the invention, the dehydro-fluorination of HFC-254fb is accomplished by reacting each of these respective intermediates with a strong caustic solution that includes, but is not limited to KOH, NaOH, LiOH, $Mg(OH)_2$, $Ca(OH)_2$, $Ca(OH)_2$, and CaO at an elevated temperature. Both a batch reactor and a CSTR can be used for carrying out this reaction. Alternatively solid metal hydroxide such as KOH pellets can be used which would allow the use of packed bed reactor.

In the preferred embodiment of the invention, the strength of the caustic solution is of from about 2 wt % to about 65 wt %, more preferably from about 5 wt % to about 52 wt %, and most preferably from about 10 wt % to about 45 wt %. The reaction is preferably conducted at a temperature of from about 20° C. to about 100° C., more preferably from about 30° C. to about 90° C. and most preferably from about 40° C. to about 80° C. The reaction is preferably conducted at atmospheric pressure, super-atmospheric pressure or under vacuum. The vacuum pressure can be from about 5 ton to about 760 torr. In addition, a phase transfer agent may optionally be used to help facilitate the reaction. This optional step may be conducted using solvents that are well known in the art for said purpose.

The fourth step can also be accomplished by the use of solid catalyst such as fluorinated chromium oxide as shown by equation (10):

(10)

As equation (10) shows, TFP is formed by the dehydrofluorination of HFC-254fb. In a preferred embodiment of the invention, the dehydrofluorination of HFC-254fb are accomplished by reacting at an elevated temperature by thermal decomposition in the presence of a catalyst. The preferred temperatures for the thermal decomposition are from about 30° C. to about 550° C., more preferably from about 300° C. to about 550° C. As above, the reaction is preferably conducted at atmospheric pressure, super-atmospheric pressure or under vacuum. The vacuum pressure can be from about 5 torr to about 760 torr.

The reaction for the dehydrofluorination of HFC-254fb (equation 10) is conducted in the presence of a dehydrofluorinating catalyst which may be one or more of fluorinated metal oxides in bulk form or supported, metal halides in bulk form or supported, and carbon supported transition metals, metal oxides and halides. Suitable catalysts include fluorinated chromia (fluorinated $Cr_2O_3$), fluorinated alumina (fluorinated $Al_2O_3$), metal fluorides (e.g., $CrF_3$, $AlF_3$) and carbon supported transition metals (zero oxidation state) such as Fe/C, Co/C, Ni/C, Pd/C.

The following examples are provided to further illustrate the invention and should not be taken as limitations of the invention.

EXAMPLE 1

A 50 gallon fluoropolymer lined reactor was charged with 75 lbs of liquid $SbCl_5$ fluorination catalyst. The reactor was equipped with a 6 inch diameter×8 feet long catalyst stripper containing structured packing and reflux condenser. The catalyst was first fluorinated by adding a sufficient amount of Hydrogen Fluoride (HF). The reactor was heated to 80° C. to 95° C. and brought to a pressure of 150 to 180 psig. Gaseous HF was fed to the reactor continuously at a rate of 23 to 28 lb/hr through a sparger and liquid HCC-240fa was fed continuously at a rate of 40 to 50 lb/hr. Chlorine gas ($Cl_2$) was continuously added to the reaction mixture to keep the catalyst active at 1.5 to 2.0 lb/hr. The gas exiting the reflux condenser was passed through a scrubber that contained KOH solution to remove excess HF and the HCl that was generated during the reaction. Several thousand lbs of the crude product was collected after the scrubber and was analyzed by GC. The following is the analysis of the major component of the crude product in GC area %. Note the presence of the HFC1234ze after the material was passed through the scrubber containing KOH solution.

EXAMPLE 1

GC Analysis

| Component | GC area % |
| --- | --- |
| 1234 | 0.1157 |
| 245fa | 92.7560 |
| 1233zd | 0.1269 |
| 244fa | 3.3879 |
| 243fa | 1.6298 |
| Others | 1.9837 |

EXAMPLE 2

The reaction system consisted of a 10 gallon jacketed Hastelloy C equipped with an agitator, a catstripper column with condenser, followed by a continuous circulated caustic scrubber (to neutralize HF and HCl), and product collection system. The reactor was initially charged with 2600 grams of $TiCl_4$ catalyst at ambient temperature and with the agitation turned on at about 200 RPM. To this was added about 3 lbs of HF, enough to completely fluorinate the catalyst plus a slight excess. The reactor was then initially charged with reactants, 13 lbs of HCC-240fa and 50 lbs of HF. The reactor temperature was slowly increased and reaction was observed at about 80° C. to 85° C. The reaction was allowed to proceed for a couple of hours with the lighter components continuously being taken overhead of the catstripper to the scrubber and product collection dry ice traps (DITs).

The HCC-240 feed was then started continuously and added into the vapor space of the reactor. The overhead take-off system was modified so that a constant amount of material was taken off the catstripper and the HCC-240fa feed rate was adjusted to match that rate. Several times during the production run the reactor was shutdown to add more HF and started up again as before. Catstripper overhead samples were taken at periodic intervals and analyzed by GC. The selectivity of the reaction for producing HCFC-244fa ranged from 47% to 57% and that of HCFO-1233zd was 40% to 50%. A total of 50 Kg of crude HCFC-244fa was produced.

In the following examples, a mixture of starting reactants is specified. These are based upon by-product analysis from other processes.

EXAMPLE 3

A reactor was constructed of 2 parallel lengths of ½ inch inner diameter stainless steel tubing. The first length was the preheater and was heated by electrical heat tape and insulated. It was packed with nickel mesh to facilitate heat transfer and mixing. The second length had a ⅛ inch profile probe inserted inside it from top to bottom. The reactor was loaded with about 21 grams (50 cc) of Aldrich 1% Pd/C catalyst and had electrical heat tape and insulation around it for heating. Prior to the experiment the catalyst was first reduced by flowing $H_2$ at 200 ml/min at room temperature and then heating to a hot spot temperature of 225° C. for 8 hours.

The hydrogenation reaction was carried out at 104° C. and 290 psig. The feed material was a mixture of HFP (hexafluoropropylene); cis-1234ze and HFC-236ea (1,1,1,2,3,3-hexafluoropropane). The feed material consisted of 7.7 GC area % HFP, 1.1 GC area % cis-1234ze and 90 GC area % of 236ea. Feed flow rate was 1.0 lb/hr. A molar ratio of $H_2$ to total olefin content of the organic feed stream was 0.5:1. The effluent from reactor contained the desired 254fb. The conversion of cis-1234ze was 98.7%. The selectivity to 254fb was in excess of 99%.

EXAMPLE 4

A second experiment was carried out with 1% Pd/C catalyst (50 ml). The feed material consisted of a mixture containing 52.4 GC area % of 245fa, 16.2 GC area % of trans-1234ze, and 31.1 GC area % of cis-1234ze. The organic feed rate was 1 lb/hr. The mol ratio of $H_2$ to the mixture of cis-1234ze and trans-1234ze was 0.73. The hot spot on catalyst bed was about 250° C. The pressure was 290 psig.

The GC analysis of reactor effluent revealed formation of 254fb. Conversion of the two 1234ze isomers combined was 70.6%. The selectivity to 254fb was >99%. It was observed that conversion of cis-1234ze was two times greater than the conversion of trans-1234ze.

EXAMPLE 5

Following the hydrogenation of cis and trans isomers of 1234ze in Example 4, the 254fb crude stream was passed through a caustic scrubber. The scrubber consisted of a sump filled with 5 wt % KOH solution. KOH solution was circulated to the top of a packed column using a pump. The KOH solution falls then through the packing by gravity and returns to the sump. The scrubber solution was held at 50° C.

The crude 254fb gas (containing previously unreacted 245fa from Example 4) was fed to the bottom of the packed column and exited at the top of the column after briefly contacting KOH solution. The gas that exited the top of the column was collected in a Product Collection Cylinder (PCC) which was placed in a Dry Ice Trap (DIT). GC analysis of the contents of the PCC revealed that 3,3,3-trifluoropropene was formed. Therefore even with relatively short contact time, TFP can be formed (1% GC area).

GC analysis of the PCC revealed the formation of some cis- and trans-1234ze. The formation of 1234ze isomers is due to dehydrofluorination of 245fa.

EXAMPLE 6

A 254fb dehydrofluorination reaction was carried out in a 1 liter Parr reactor. The reactor was loaded with 466.6 g of 25% KOH and 183.1 g of 254fb crude material produced in Example 4. The feed mixture consisted of 10.1 GC area % 1234ze, 1.8 GC area % 236ea, 50.7 GC area % 245fa, 6.4 GC area % cis-1234ze, 29.6 GC area % 254fb, and smaller amounts of unidentified components. The reactor was heated to about 60° C. After 9 hours of hold time, the pressure gradually rose to 160 psig (initial pressure was 30 psig).

The reactor contents were transferred into product collection cylinder (PCC) that was placed in dry ice. GC analysis of PCC revealed that 1243zf was formed. Conversion of 254fb was 69.0%. GC analysis also revealed that 245fa amount decreased after reaction and that amount of 1234ze isomers increased. Analysis of spent KOH solution revealed that the strength of KOH remaining was only 3.2%.

EXAMPLE 7

A 254fb dehydrofluorination reaction was carried out in the same fashion as in Example 6, except that reactor was loaded with 451 g of 25% KOH and 192.3 g of feed material. Heating the reactor to 60° C. led to pressure an increase of 100 psig. Reactor temperature peaked at about 63° C. After 9 hours, the contents of the reactor were transferred to the PCC.

GC analysis of the PCC revealed that 1243zf was formed. Conversion of 254fb was 66.4% GC analysis also revealed that 245fa amount decreased after reaction and that amount of 1234ze isomers increased. Analysis of spent KOH solution revealed that the strength of KOH remaining was only 3.15%.

EXAMPLE 8

This example illustrates the continuous vapor phase dehydrochlorination reaction of HCFC-244fa to HFO-1234ze+HCl. The dehydrochlorination catalyst for the experiment is 10 wt % CsCl/90 wt % MgF$_2$.

Conversion of HCFC-244fa into HFO-1234ze is performed using a Monel reactor (inner diameter 2 inches, length 32 inches) equipped with a Monel preheater (inner diameter 1 inch, length 32 inches) which is filled with Nickel mesh to enhance heat transfer. The reactor is filled with 2.0 liters of pelletized 10 wt % CsCl/90 wt % MgF$_2$ dehydrochlorination catalyst. Nickel mesh is placed at the top and at the bottom of reactor to support the catalyst. A multi-point thermocouple is inserted at the center of the reactor to monitor the catalyst bed temperature. The catalyst is pretreated in dry N$_2$ flow for 6 hours at the temperature of 480° C.

A feed mixture containing 98.0 GC % HCFC-244bb; 0.9 GC % HCFO-1233zd and 1.1 GC % HFC-245fa is then introduced into the reactor at the rate of 1.0 lb/hr. The feed is vaporized prior to entering the reactor preheater. The feed rate is maintained constant at 1.0 lbs/hr and both temperature and pressure are varied. The productivity range of the catalyst is estimated at 3 to 6 lbs/hr/ft$^3$. The highest productivity is observed at 470° C. and 45 psig, and the lowest productivity is observed at 480° C. and 3 psig. The reaction products are passed through a caustic scrubber to remove HCl by-product. Then the product stream is passed through a column filled with desiccant to remove residual moisture and collected in a cold trap.

Reaction Data

| | |
|---|---|
| 480° C. at 3 psig | HCFC-244fa conversion, about 30% |
| | Selectivity to HFO-1234ze, about 97% |
| 480° C. at 20 psig | HCFC-244fa conversion, about 47% |
| | Selectivity to HFO-1234ze, about 96% |
| 470° C. at 20 psig | HCFC-244fa conversion, about 36% |
| | Selectivity to HFO-1234ze, about 97% |
| 470° C. at 45 psig | HCFC-244fa conversion, about 53% |
| | Selectivity to HFO-1234ze, about 96% |
| 460° C. at 45 psig | HCFC-244fa conversion, about 38% |
| | Selectivity to HFO-1234ze, about 99% |

EXAMPLE 9

539.5 grams of 9.3 wt % KOH solution and 135.4 grams of 90.0 GC area % pure 1-chloro-1,3,3,3-tetrafluoropropane (HCFC-244fa) were added to a 1.0 liter stainless steel (SS) cylinder. The other major component in this reaction mixture was HCFC-1223xd (1,2-dichloro-3,3,3-trifluoropropene) which amounted to 9.2 GC area %. The cylinder was heated to 75° to 80° C. and shaken for five (5) hours.

A sample of the vapor space showed the presence of 75.6 GC area % HFC-1234ze trans isomer, 12.9 GC area % HFC-1234ze cis isomer, 8.5 GC area % HCFC-244fa, and 0.8 GC area % HCFC-1223xd. A sample of the organic liquid phase showed 24.4 GC area % HFC-1234ze trans isomer, 12.9 GC area % HFC-1234ze cis isomer, 44.2 GC area % HCFC-244fa, and 8.1 GC area % HCFC-1223xd.

560.0 grams of aqueous solution was collected after the experiment which amounts to a weight gain of 20.5 grams in the aqueous layer. Assuming this weight gain is HCl that was produced during the dehydrochlorination of 244fa it can be calculated that about a 60% conversion of HCFC-244fa to HFC-1234ze occurred during the reaction.

EXAMPLE 10

A reaction mixture consisting of 91.5 GC area % HFC-245fa and 0.0121 GC area % HFC-1234ze was bubbled through a 2.0 wt % potassium hydroxide (KOH) solution. The organic mixture resulting from the combination was collected and analyzed by GC equipped with a FID. The mixture contained 15.455 GC area % HFO-1234ze (cis+trans).

EXAMPLE 11

HFC-245fa Dehydrofluorination Over Selected Catalysts

Three different kinds of catalysts, namely, fluorinated metal oxide, metal fluoride(s), and supported metal, were used for 245fa dehydrofluorination in Example 11. In each case, 20 cc of catalyst was used. A 100% 245fa feed was flowed over catalyst at a rate of 12 g/h. As shown in Table 1, all the catalysts listed in Table 1 exhibited a high activity (>80% 245fa conversion) and a high selectivity to cis/trans-1234ze (>90%) during 245 dehydrofluorination.

TABLE 1

HFC-245fa dehydrofluorination over various catalysts

| Catalyst | Temp °C. | HFC-245fa Conversion % | Trans-1234ze Selectivity % | cis-1234ze selectivity % | Others* selectivity % | Catalyst productivity lbs/hr/ft³ |
|---|---|---|---|---|---|---|
| Fluorinated $Cr_2O_3$ | 350 | 96 | 80.6 | 18 | 1.4 | 26 |
| $AlF_3$ | 350 | 96.8 | 80.4 | 16.3 | 3.3 | 26.2 |
| 10% $MgF_2$—90% $AlF_3$ | 350 | 98.3 | 78.6 | 17.5 | 4 | 26 |
| Fe/AC | 525 | 80 | 67.8 | 23.4 | 8.8 | 18.2 |

Reaction conditions: 20 cc catalyst, 12 g/h 245fa, 1 atm.
*Others include 2,3,3,3-tetrafluoropropene, 3,3,3-trifluoropropyne, etc.

EXAMPLE 12

HFC-254fb Dehydrofluorination Over Selected Catalysts

The same experiments with the same dehydrofluorination catalysts are repeated using 254fb instead of 245fa. Three different kinds of catalysts, namely, fluorinated metal oxide, metal fluoride(s), and supported metal, are used for 254fb dehydro-fluorination in Example 12. In each case, 20 cc of catalyst is used. A 100% 254fb feed is flowed over catalyst at a rate of 12 g/h. Results are similar to those of Example 11, but 1243zf is the product produced.

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A process for the preparation of 3,3,3-trifluoropropene comprising the steps of:
    (a) fluorination of HCC-240fa to form HFC-245fa;
    (b) dehydrofluorination of HFC-245fa to form a cis/trans mixture of HFO-1234ze;
    (c) hydrogenation of the cis/trans mixture of HFO-1234ze to form HFC-254fb; and
    (d) dehydrofluorination of HFC-254fb to produce 3,3,3-trifluoropropene.

2. The process of claim 1, wherein the compound HFC-245fa is formed by the fluorination of HCC-240fa with HF in the presence of a fluorination catalyst.

3. The process of claim 2, wherein the fluorination catalyst comprises a pentavalent antimony fluorination catalyst.

4. The process of claim 3, wherein the pentavalent antimony catalyst is selected from the group consisting of antimony halides, mixed pentavalent antimony halides, and a mixture of pentavalent antimony halides.

5. The process of claim 3, wherein the pentavalent antimony catalyst is selected from the group consisting of antimony pentachloride and antimony pentafluoride.

6. The process of claim 3, wherein the pentavalent antimony catalyst is antimony pentachloride.

7. The process of claim 1, wherein the dehydrofluorination reaction of HFC-245fa takes place in the presence of a metal hydroxide.

8. The process of claim 7, wherein the metal hydroxide is selected from the group consisting of KOH, NaOH, LiOH, $Mg(OH)_2$, $Ca(OH)_2$, and CaO.

9. The process of claim 7, wherein the metal hydroxide is in solution.

10. The process of claim 7, wherein the metal hydroxide is in solid form.

11. The process of claim 1, wherein the dehydrofluorination reaction of HFC-245fa takes place in the presence of a catalyst.

12. The process of claim 11, wherein the catalyst is selected from the group consisting of one or more of fluorinated metal oxides in bulk form or supported, metal halides in bulk form or supported, and carbon supported transition metals, metal oxides and halides.

13. The process of claim 11, wherein the catalyst is selected from the group consisting of fluorinated chromia, fluorinated alumina, metal fluorides, and carbon supported transition metals with zero oxidation state.

14. A process for the preparation of 3,3,3-trifluoropropene comprising the steps of:
    (a) fluorination of HCC-240fa to form HCFC-244fa;
    (b) dehydrochlorination of HCFC-244fa to a cis/trans mixture of HFO-1234ze;
    (c) hydrogenation of the cis/trans mixture of HFO-1234ze to form HFC-254fb; and
    (d) dehydrofluorination of HFC-254fb to produce 3,3,3-trifluoropropene.

15. The process of claim 14, wherein the fluorination reaction takes place with HF in the presence of $TiCl_4$.

16. The process of claim 14, wherein the dehydrochlorination reaction takes place in the presence of a metal hydroxide.

17. The process of claim 16, wherein the metal hydroxide is selected from the group consisting of KOH, NaOH, LiOH, $Mg(OH)_2$, $Ca(OH)_2$, and CaO.

18. The process of claim 16, wherein the metal hydroxide is in solution.

19. The process of claim 16, wherein the metal hydroxide is in solid form.

20. The process of claim 14, wherein the dehydrochlorination reaction takes place in the presence of a catalyst.

21. The process of claim 20, wherein the catalyst is selected from the group consisting of one or more of supported or bulk metals of Pd, Pt, Rh, Fe, Co, Ni, Cu, Mo, Cr, Mn, magnesium halides, calcium halides, lithium halides, sodium halides, potassium halides, cesium halides, cerium halides, yttrium halides, aluminum halides, halogenated magnesium oxides, halogenated calcium oxides, halogenated barium oxides, halogenated zinc oxides, halogenated cesium oxides, halogenated aluminum oxide, and combinations thereof.

22. The process of claim 20, wherein the catalyst is selected from the group consisting of one or more of supported or bulk catalysts selected from the group consisting of MgO, CaO, BaO, ZnO, CsO, $Al_2O_3$, LiF, NaF, KF, CsF, $MgF_2$, $CaF_2$, LiCl, NaCl, KCl, $CeF_4$, $FeF_3$, $YF_3$, $AlF_3$ and CsCl.

23. The process of claim 20, wherein the catalyst is selected from the group consisting of a combination of CsCl and MgO, and/or a combination of CsCl and $MgF_2$.

24. The process of claim 1 or 14, wherein the hydrogenation of the cis/trans mixture of HFO-1234ze to form HFC-254fb takes place in the presence of catalyst.

25. The process of claim 24, wherein the hydrogenation catalyst is selected from the group consisting of Pd on carbon, $Pd/Al_2O_3$, Ni/C, and $Ni/Al_2O_3$.

26. The process of claim 1 or 14, wherein the dehydrofluorination reaction of HFC-254fb is conducted in the presence of a metal hydroxide.

27. The process of claim 26, wherein the metal hydroxide is selected from the group consisting of KOH, NaOH, LiOH, $Mg(OH)_2$, $Ca(OH)_2$, and CaO.

28. The process of claim 26, wherein the metal hydroxide is in solution.

29. The process of claim 26, wherein the metal hydroxide is in solid form.

30. The process of claim 1 or 14, wherein the dehydrofluorination reaction of HFC-254fb takes place in the presence of a catalyst.

31. The process of claim 30, wherein the catalyst is selected from the group consisting of one or more of fluorinated metal oxides in bulk form or supported, metal halides in bulk form or supported, and carbon supported transition metals, metal oxides and halides.

32. The process of claim 30, wherein the catalyst is selected from the group consisting of fluorinated chromia, fluorinated alumina, metal fluorides, and carbon supported transition metals with zero oxidation state.

\* \* \* \* \*